United States Patent [19]

Altinger et al.

[11] Patent Number: 5,788,895
[45] Date of Patent: Aug. 4, 1998

[54] MASS TRANSFER IN PLATE COLUMNS AND APPARATUS FOR THIS PURPOSE

[75] Inventors: Gerhard Altinger, Speyer; Horst Egly, Böhl-Iggelheim; Rudolf Kaiser; Fritz Thiessen, both of Ludwigshafen, all of Germany

[73] Assignee: BASF Aktiengesellschaft, Ludwigshafen, Germany

[21] Appl. No.: 692,189

[22] Filed: Aug. 5, 1996

[30] Foreign Application Priority Data

Aug. 17, 1995 [DE] Germany ............ 195 30 291.5

[51] Int. Cl.$^6$ ............ B01F 3/04
[52] U.S. Cl. ............ 261/114.5; 261/113
[58] Field of Search ............ 261/114.5, 113

[56] References Cited

U.S. PATENT DOCUMENTS

| 2,860,860 | 11/1958 | Wilson | 261/113 |
| 3,759,497 | 9/1973 | Black | 261/114.5 |
| 4,032,410 | 6/1977 | Kuxdorf et al. | 261/114.5 |
| 4,133,852 | 1/1979 | DiNicolantonio et al. | 261/114.5 |
| 4,174,363 | 11/1979 | Bruckert | 261/114.1 |
| 4,876,037 | 10/1989 | Leva | 261/114.5 |
| 5,547,617 | 8/1996 | Lee et al. | 261/114.5 |

FOREIGN PATENT DOCUMENTS

| 1946159 | 9/1969 | Germany. |
| 1542242 | 4/1970 | Germany | 261/114.5 |
| 30 45 857 | 12/1980 | Germany. |
| 32 47 813 | 12/1982 | Germany. |

Primary Examiner—Tim R. Miles
Attorney, Agent, or Firm—Keil & Weinkauf

[57] ABSTRACT

Column tray for a mass transfer column, in particular one provided with a support ring at the circumference, which tray has support elements and tray plates arranged side by side on the support elements and having passages, in particular holes, valves or bubble caps, wherein the majority, preferably the total number, of tray plates are connected liquid-tight, preferably welded, to the support elements or the support ring, in particular in discrete area elements; the majority, preferably the total number, of support elements are connected liquid-tight, preferably welded, to one another and to the column wall or the support ring, in particular in discrete area elements; and in addition the majority, preferably the total number, of adjacent tray plates and support elements are separated from one another and from the column wall or the support ring by gaps having a width of from 1 to 15 mm, preferably from 1 to 7 mm.

3 Claims, 3 Drawing Sheets

MASS TRANSFER IN PLATE COLUMNS AND APPARATUS FOR THIS PURPOSE

The present invention relates to an apparatus and a process for mass transfer between liquids and gases in plate columns. In particular, a special embodiment of column trays is proposed.

Plate columns are now used for a large number of mass transfer processes between liquids and gases. The liquid flows over the column tray, which has a large number of orifices. Gas is fed into the liquid through these orifices, so that the mass transfer process can take place. The liquid is passed on from tray to tray through the orifices or through special removal means.

Many possible forms of tray orifices are known. Flat orifices may be provided (sieve trays; dual-flow trays), the orifices may be provided with valves (valve trays) and the orifices may also be shielded from the liquid by bubble caps (bubble trays). Also known are more highly integrated tray forms, such as tunnel and centrifugal trays, in which an increasing number of orifices are combined to form a group of gas inlets and in which the direction of liquid flow is controlled by the momentum of the outflowing gas.

In the plate columns used today, which have diameters of several meters, the trays are composed of a plurality of plates which are mounted or fastened on supports or on support elements, such as an edge ring or individual mounting pieces on the column wall.

The tray plates fastened to supports are positioned flush with one another and screwed together with the aid of clamps or clamping strips. In other embodiments, the tray plates are arranged in an overlapping manner or wedges are inserted from above into the gaps between the tray plates. In addition to increasing the strength of the tray structure, all these measures are intended to prevent the passage of liquid between the tray plates instead of at the liquid discharges provided. This additional uncontrolled liquid discharge is undesirable even in the case of ripple trays or turbogrit trays in which the liquid flows away through gas feed orifices.

In all stated designs, very fine passages, in particular capillary gaps (hairline gaps), form at the connection lines of tray plates with one another or with support elements (supports) or at screw unions of tray parts. In such fine passages, the residence time of the liquid is many times longer than the average residence time of a liquid volume on a column tray. In the case of certain substances, this leads to polymerization, coagulation, caking or other undesirable physical or chemical changes. Frequently, the hairline gaps are only the starting point for such reactions, which then continue on the column tray.

The hairline gaps are also neuralgic points with regard to the collection of undesirable substances (dirt), particularly owing to the difficulty of cleaning at these points. These design-related hairline gaps are therefore also the starting point and cause of a number of contamination, caking and polymerization problems.

It has not been technically possible to date, at an acceptable cost, to prevent the formation of fine passages, in particular of capillary gaps, between the components of a column tray. Neither more exact fits nor higher contact pressures through a tighter screw union or riveting nor the introduction of sealing compounds lead to a solution to this problem. The last-mentioned present problems in a column tray in particular because the vibrations of the tray structure due to the gas flow have a very adverse effect on the adhesion of sealing compounds in joints.

It is an object of the present invention to provide a column tray for installation in a mass transfer column and a process for mass transfer in a plate column, in which polymerization, coagulation, caking, contamination and other physical or chemical changes in fine passages between the components of the column tray are avoided.

We have found that this object is achieved by the column trays described in the claims. A novel column tray for a mass transfer column provided in particular with a support ring at the circumference consists of support elements and tray plates arranged side by side on the support elements and having passages, in particular holes, valves or bubble caps. In the novel column tray, the majority, preferably the total number, of tray plates are connected liquid-tight, preferably welded, to the support elements or the support ring; the majority, preferably the total number, of support elements are connected liquid-tight, preferably welded, to one another and to the column wall or the support ring; and in addition the majority, preferably the total number, of adjacent tray plates and support elements are separated from one another and from the column wall or the support ring by gaps having a width of from 1 to 15 mm, preferably from 1 to 7 mm. Thus, the formation of undesirable gaps is counteracted by the fact that, on the one hand, the gaps are made sufficiently large to avoid the disadvantageous reactions described and, on the other hand, small areas are sealed so well that gap formation can be avoided with acceptable technical complexity. The production of small-area weld joints between the components to be connected is particularly beneficial since this makes it possible to provide a liquid-tight connection in an advantageous manner.

This novel design should as far as possible be chosen for all contact surfaces of tray plates, support elements and the column wall or a support ring at the column wall. Of course, the design of the predominant number of contact surfaces is sufficient to lead to a positive result according to the invention. For other reasons, however, it may be advantageous to choose other types of connection, for example a screw union, at certain points, for example at ladders.

Preferably, the majority, in particular the total number, of tray plates are connected, in particular welded, to viaduct-like support elements. The viaduct arches are open toward the tray plates so that the mass transfer is not divided into tray segments but the liquid can flow very freely on the column tray. Moreover, the use of viaduct arches welded to the feet leads to a light support or bearing structure.

A column tray whose proportion by area of the gaps present in the tray plane is not more than 15% of the total orifice ratio is preferred. The total orifice ratio is defined as a proportion of the gas-permeable area (gaps, passages) in the tray plane relative to the total area of the tray plane (column cross-section). The area of discharge shafts is not included in the calculation, since no mass transfer takes place there. A column tray which is designed as a dual-flow tray and is arranged in the mass transfer column is particularly preferred. The combination with the viaduct arches described above is particularly advantageous.

We have found that the object according to the invention is also achieved by the mass transfer process, described in the claims, in a plate column. Liquid is moved in the tray plane on a column tray which has support elements and tray plates arranged side by side on the support elements and having passages, in particular holes, valves or bubble caps, and gas is fed to the liquid through the passages, wherein the majority, preferably the total number, of tray plates are connected liquid-tight, preferably welded, to the support elements or the support ring; the majority, preferably the total number, of support elements are connected liquid-tight, preferably welded, to one another and to the column wall or the support ring; and in addition the majority, preferably the total number, of adjacent tray plates and support elements are separated from one another and from the column wall or the support ring by gaps having a width of from 1 to 15 mm, preferably from 1 to 7 mm.

A preferred process is one in which the majority, preferably the total number, of tray plates are connected, in particular welded, to viaduct-like support elements, the viaduct arches being open toward the tray plates.

Another preferred process is one in which the gaps in the tray plane are arranged and dimensioned in such a way that their proportion by area is not more than 15% of the total orifice ratio.

A further preferred process is one in which liquid and gas are combined according to the dual-flow principle in a liquid-gas jet.

According to the invention, a mass transfer column which has at least one column tray described in the claims is also provided.

In accordance with the object of the present invention, a process for the production of a column tray for a mass transfer column is also provided, tray plates having passages, in particular holes, valves or bubble caps, being arranged side by side on support elements or on the support ring, wherein the majority, preferably the total number, of tray plates are connected liquid-tight, preferably welded, to the support elements or the support ring, and the majority, preferably the total number, of support elements are connected liquid-tight, preferably welded, to one another and to the column wall or the support ring. In addition, the majority, preferably the total number, of adjacent tray plates and support elements are separated from one another and from the column wall or the support ring by gaps having a width of from 1 to 15 mm, preferably from 1 to 7 mm.

A preferred production process is one in which the majority, preferably the total number, of tray plates are connected, in particular welded, to viaduct-like support elements, the viaduct arches being open toward the tray plates.

A further preferred process is one in which the tray plates having passages are designed and are arranged in the plate column in such a way that the proportion by area of the gaps present in the tray plane is not more than 15% of the total orifice ratio.

Such column trays are preferably designed and arranged in the mass transfer column as dual-flow trays.

In the case of the plate columns and processes described in the claims, the passage of liquid through capillary gaps, ie. gaps having a width of less than 0.5 mm, is to be prevented. For this purpose, it is necessary either completely to avoid gaps at connections between plates and holding means or to make said gaps sufficiently large for the liquid to pass through substantially unhindered. Tests have shown that the fluid dynamic behavior of the novel tray design has only slight disadvantages in comparison with the conventional tray design. These disadvantages are minimal in particular in the case of the viaduct-like design of the support elements which is described above.

BRIEF DESCRIPTION OF THE DRAWINGS

The invention is illustrated below with reference to three Figures.

DETAILED DESCRIPTION OF THE DRAWINGS

Figure 1:
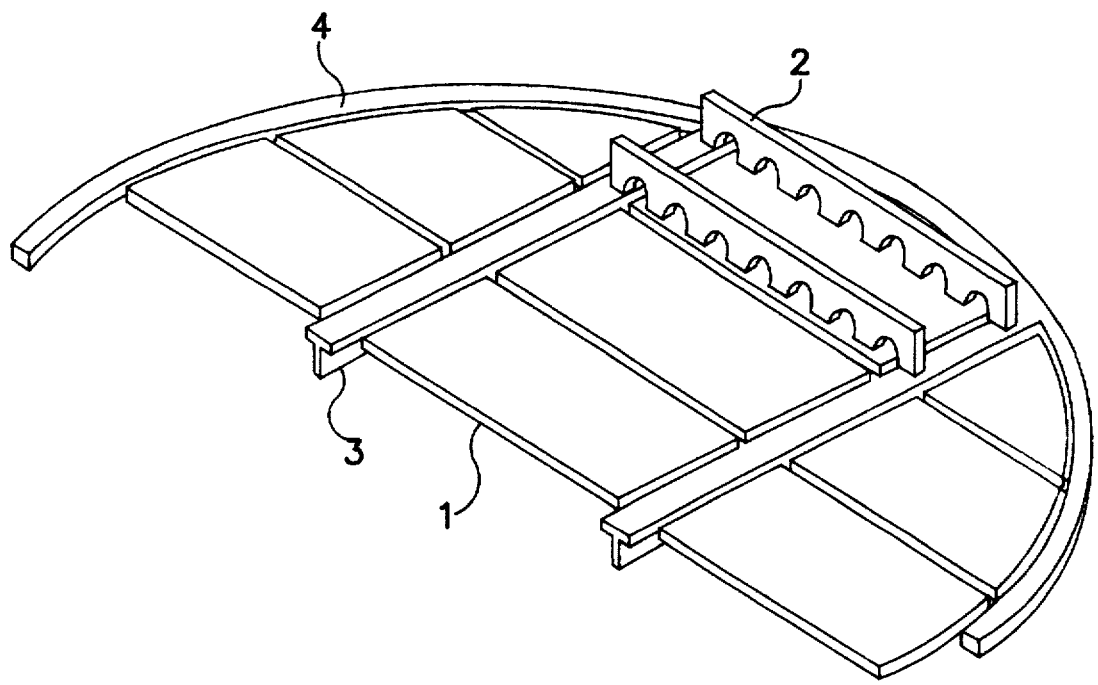
FIG. 1: Diagram showing the principle of a novel column tray.

FIG. 1 shows a novel column tray. The tray plates 1 are held by viaduct-like support elements 2, each of which is welded to the tray plates and the other support elements (bearers) 3 and to the support ring 4 attached to the column wall. In addition, gaps having a width of about 5 mm are present between the tray plates themselves, between the tray plates and the support elements and between the support elements themselves and between the support elements and the support ring. Depending on the column diameter, larger or smaller scatters of the gap width are obtained due to the production. In order to avoid capillary gaps, the gap width must not be less than 1 mm.

Figure 2:
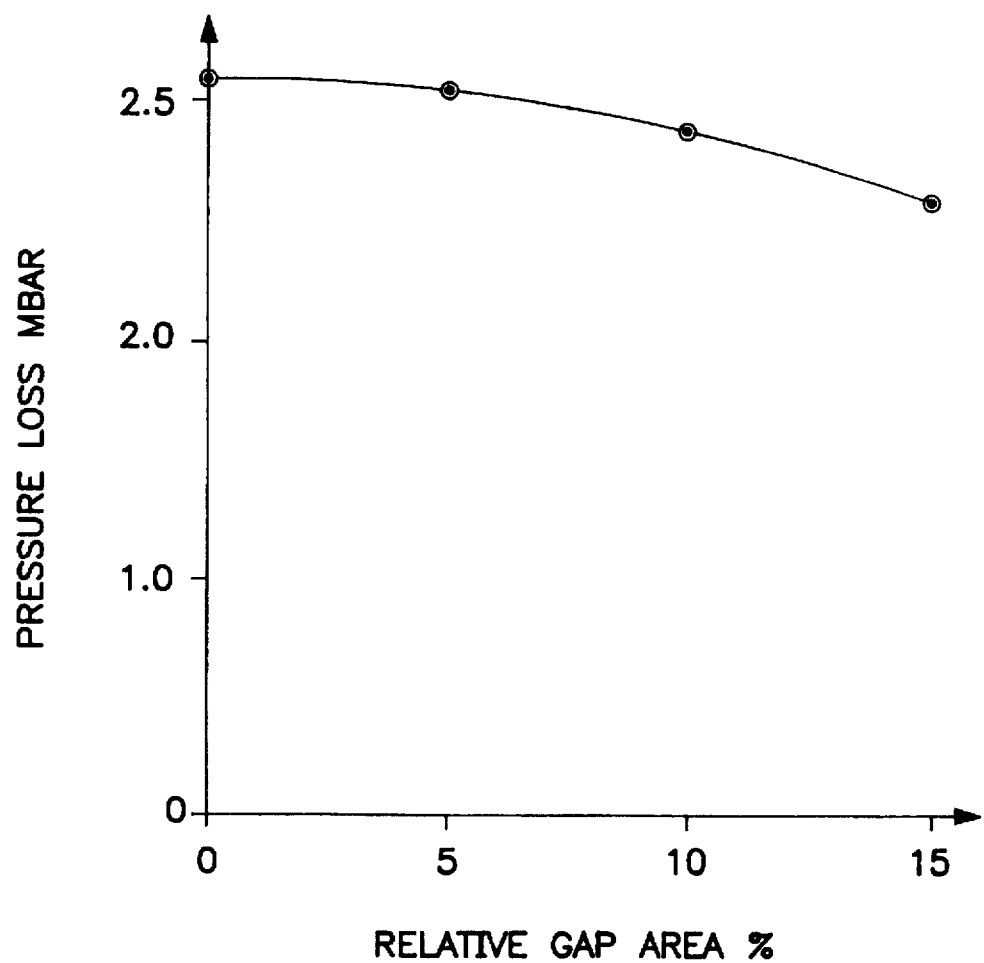
FIG. 2: Pressure loss of a novel column tray (dual-flow tray) as a function of the relative gap area.

FIG. 2 shows the pressure loss of a dual-flow tray in mbar as a function of the relative gap area. The relative gap area is understood as meaning the ratio of the gap area in the tray plane to the total area in the tray plane through which liquid can pass (gaps, holes, etc.).

The measured curves were recorded for dual-flow trays in a column having a diameter of 2500 mm. The hole diameter was 14 mm, the gap width 5 mm, the tray thickness 5 mm and the total orifice ratio was maintained at 13.2% by varying the number of holes. A 40 mm wide support ring was present on the column wall. Three dual-flow trays were mounted a distance of 400 mm apart. A distributor tray was also installed. The measurements were carried out with water and air at the middle tray. Water was introduced in an amount of 3.6 $m^3/m^2h$ and air in each case in an amount corresponding to a flow velocity of 1.1 m/s.

It was found that the pressure loss decreased with increasing relative gap area. It was therefore intended to provide only the number of gaps required for satisfactory functioning for the purposes of the present invention, ie. for avoiding coagulation and contamination.

Figure 3:
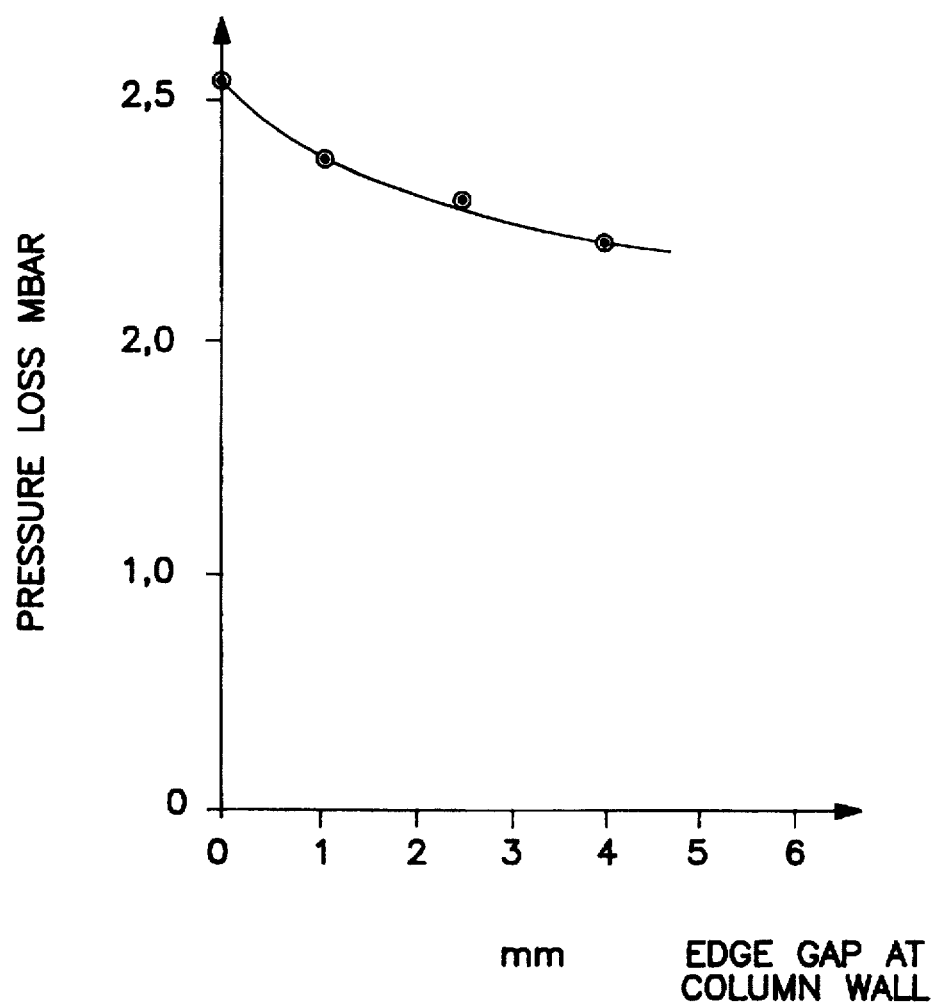
FIG. 3: Pressure loss of a novel column tray as a function of the diameter of the annular wall gap.

FIG. 3 shows the dependence of the pressure loss in mbar on the width of the annular gap along the column wall.

Instead of gaps between the individual components, a single edge gap at the column wall which was interrupted only by a few necessary holders for the column trays was provided here for demonstration purposes. The column diameter was 2500 mm, the hole diameter 14 mm and the tray thickness 5 mm. The water and air supply and the measurement of the pressure loss corresponded to the procedure described under FIG. 2. The total orifice ratio was once again kept constant at 13.2% by varying the number of holes.

It was found that the pressure loss decreased greatly with increasing edge gap width. It is therefore advantageous to keep an edge gap at the column wall so small that the function according to the invention is just performed. In the interests of effective mass transfer, an annular gap at the column wall is completely avoided.

EXAMPLE

A typical example of the use of a column tray designed according to the invention is the separation of acrylic acid from byproducts. Here, polymer forms on the distillation trays in industrial distillation columns in spite of the addition of stabilizers.

This process is due in particular to the long residence time of the acrylic acid in fine gaps, in particular in capillary gaps. The formation and the growth of polymer and the deposition of dirt are thus promoted.

This can be illustrated by a simple experiment. Acrylic acid is allowed to run on the one hand over a screw on which a washer is fixed with a nut and at the same time over a flat metal plate. After from 5 to 8 days, clearly visible polymer is present on the screw and nut, whereas such deposits are not detectable on the flat metal plate.

The acrylic acid used in the experiment was stabilized with 200 ppm of phenothiazine. This was a crude acrylic acid which had been obtained by catalytic gas-phase oxidation of acrolein according to Example B1 of DE 43 02 991 and by subsequent working up of the reaction gases according to Example B1 of DE 21 36 396.

We claim:

1. A column tray for a mass transfer column having a circumference, said mass transfer column further having a wall and a support ring at the circumference, said tray having support elements and tray plates arranged adjacent to each other and further having passages for the passage of gas, wherein the majority of the tray plates are connected liquid-tight to the support elements, and the majority of support elements are connected liquid-tight to one another and the column wall or the support ring, and the majority of adjacent tray plates and support elements are separated from one another and the column wall by gaps having a width of from 1 to 15 mm, wherein the majority of tray plates are connected to viaduct-like support elements having arches, said arches being open toward the tray plates.

2. A column tray as claimed in claim 1, wherein the proportion by area of the gaps present in the tray plate is not more than 15% of the total orifice ratio, wherein a liquid and gas are combined in said gaps according to the dual-flow principle to form a stream which contains liquid and gas.

3. A column tray as claimed in claim 1, which is a dual-flow tray and is arranged in the mass transfer column.

* * * * *